United States Patent [19]
Policastro

[11] Patent Number: 5,309,925
[45] Date of Patent: May 10, 1994

[54] DIFFUSE REFLECTIVE LASER BARRIER

[75] Inventor: Peter P. Policastro, Coral Springs, Fla.

[73] Assignee: Med-Genesis, Inc., Miami, Fla.

[21] Appl. No.: 76,792

[22] Filed: Jun. 15, 1993

[51] Int. Cl.⁵ .............................................. A61B 19/00
[52] U.S. Cl. ......................................... 128/849; 606/2
[58] Field of Search ................................ 128/849–856; 219/121.6, 121.82, 121.85; 340/557, 600; 606/2

[56] References Cited

U.S. PATENT DOCUMENTS

| | | |
|---|---|---|
| 4,558,093 | 12/1985 | Hatzenbuhler ...................... 128/849 |
| 4,616,641 | 10/1986 | Teeple . |
| 4,635,625 | 1/1987 | Teeple . |
| 4,646,734 | 3/1987 | Cabrera et al. . |
| 4,715,366 | 12/1987 | Teeple . |
| 4,735,623 | 4/1988 | Hatzenbuhler ...................... 128/846 |
| 4,901,738 | 2/1990 | Brink et al. . |
| 4,938,233 | 7/1990 | Orrison ................................ 128/849 |
| 5,014,723 | 5/1991 | Kaufman ............................. 128/849 |
| 5,033,479 | 7/1991 | Tanny ................................. 128/846 |
| 5,151,095 | 9/1992 | Teeple ................................ 128/849 |
| 5,212,387 | 5/1993 | Swan .................................. 128/849 |

*Primary Examiner*—Michael A. Brown
*Attorney, Agent, or Firm*—Clyde I. Coughenour

[57] ABSTRACT

A reflective metallic foil is modified so that an incident laser beam is diffused into multiple beams to dissipate the energy of the incident beam. The surface can have protrusions that range from 0.3 to 10,000 microns high with an average diameter of from 1 to 1,000 microns and an average spacing between protrusions of from 0.2 to 5,000 microns. The surface of the metallic foil can be provided with a first type pattern consisting of protrusions and indentations having an optimum range of 0.3 to 20 microns deep having average optimum diameter of 2 to 40 microns with an average optimum spacing between protrusions of 1 to 100 microns or a second type pattern consisting of protrusions and indentations having an optimum range of 20 to 100 microns deep having an average optimum diameter of 20 to 100 microns with an average optimum spacing of from 20 to 200 microns. The second type pattern can be superimposed on patterns of the first type.

20 Claims, 3 Drawing Sheets

DIFFUSE REFLECTIVE LASER BARRIER

CROSS-REFERENCE

The subject matter of this application is related to that of applicant's co-pending application Ser. No. 08/002,668 filed 11 Jan. 1993.

BACKGROUND OF THE INVENTION

1. Field of the Invention

The invention is to a new laser beam reflector dispersion means in combination with a gauze for use as a shield during laser surgery, or other laser use, to protect persons and/or equipment in the vicinity by dissipating the beam energy in multiple directions.

2. Description of the Related Art

Laser usage has greatly proliferated over the past decade because of the many advantages the laser offers over the scalpel. The laser beam can be pin-pointed in its placement with great accuracy; it cuts without pressure; and it seals off blood vessels upon cutting, thereby greatly reducing the quantity of blood loss during surgery. The laser also represents a greater complexity and danger that must be dealt with effectively in the clinical setting. Safety has become a major concern when working with lasers and more powerful lasers continue to be developed. Numerous accounts of accidents with medical lasers during surgical procedures have been reported by the FDA and others. Injuries to the eye causing blindness is the most frequent devastating accident. Damage to the skin and other body organs has also frequently occurred. Laser beams that are reflected as highly collimated beams off smooth metallic surfaces, typical of surgical instruments and other objects found in the operating room, have been a particular problem that has resulted in serious injuries.

The most common method of protecting the patient from exposure to laser radiation in the operating room is by employing a surgical drape of towels or gauze pads that have been saturated with water or other suitable aqueous solutions, such as saline solutions. The wetted towels or gauze pads are applied adjacent the wound site, or locus of impact, where the surgeon intends to direct the laser beam, with the towel or gauze surrounding the wound site. Only the area to be operated on is left exposed. Additionally, in surgical procedures in the region of the head or neck, or whenever the patient undergoes general anesthesia, the patient's eyes are normally protected by draping the eyes with wetted towels or gauze pads. The time period over which wet towels or gauze pads provide protection depends on the type of laser and the power density of the laser beam. In many cases, the duration of effective protection against laser exposure is less than one second. When using typical power density carbon dioxide lasers, water in the towels is evaporated rapidly. Once the water is evaporated, the drape is no longer effective to protect the underlying tissue. During lengthy operating room procedures, water continually evaporates from the wetted gauze or towel dressings under ambient conditions, reducing the level of protection that was initially provided. When using the shorter wavelength lasers, the radiation is not effectively blocked or absorbed by the wet towel or gauze; it is transmitted to the underlying tissue. Exposure of tissue to the laser can result in serious injury to the patient.

Protective articles have been described in the prior art which seek to improve levels of safety in the operating room during laser surgical procedures. U.S. Pat. No. 4,616,641, issued 14 Oct. 1986 to E. Teeple, describes a surgical shield for use during laser surgical procedures comprised of a fabric sheet positioned between a pair of coextensive metal foil sheets. The preferred inner sheet is cotton gauze and the outer sheets are aluminum foil, with at least one of the foil sheets having an outer matte surface finish. The nature of the matte finish and method of its formation are not described. U.S. Pat. No. 4,635,625, issued 13 Jan. 1987 to E. Teeple, describes a surgical eye mask for use during laser treatment having an outer layer made from a metallic foil to which are secured a pair of gauze eye pads. The metallic foil is disclosed as being "highly reflective" and is intended to be the outer layer of the mask which is first to contact the laser beam. U.S. Pat. No. 4,901,738, issued 20 Feb. 1990 to R. Brink et al, describes a laser shield with an opaque, flexible, fabric sheet having one major surface with a reflective metal foil. The opaque, flexible, fabric sheet represents the outer layer, incident to the laser beam, and the foil represents an immediately underlying layer. The foil has a thickness sufficient to resist puncture by a carbon dioxide laser using 20 watts of power for at least one second. One function ascribed to the flexible fabric sheet is to reduce reflection of the beam. However, since the fabric sheet is rapidly penetrated by the laser beam, exposing the "shiny" metallic surface, protection from the reflected laser beam is very brief and may not be adequate to avert injury from exposure to the reflected beam.

In applicant's co-pending application, a laser barrier of a "gas blown" silicone foam sheet which optionally may contain an underlying layer of metallic foil is disclosed. That laser barrier has demonstrated being effective in stopping penetration of laser beams and of not externally reflecting the laser beam. It provides protection to the patient or underlying object as well as protecting persons or objects from reflected beams. Although that laser barrier is highly useful for many surgical procedures, the cost of the barrier limits its applications, especially for relatively low cost minor surgical and dental procedures where a laser is utilized. Also, the chemical and physical changes which occur to the laser barrier upon impact with the laser beam, cause a reduction in flexibility. Because of this, the barrier is not ideally suited for certain surgical procedures such as a minimally invasive laser surgical procedures which are accomplished within the body cavity without the need for large incisions. In such minimally invasive procedures, the barrier must remain flexible so that it can be passed through the small opening of the body wall after the surgery is completed.

Prior art laser barrier articles do not offer adequate combined protection of both the patient and the operating room staff. The "highly reflective" metallic foil protects the patient but endangers those in the operating room by virtue of specular reflection. Reducing the reflective nature of a thin metal layer by changing the molecular nature of the surface of the metal, such as by anodization, result in absorption of the beam on the surface, followed by meltdown and penetration of the thin metal layer. Application of nonreflective coatings to a thin metal layer surface, also results in absorption of the beam on the surface followed by meltdown and penetration. Applying a fabric layer on the outer surface of a thin metal layer provides only very brief protection before the fabric is vaporized and the exposed shiny metal layer reflects the beam.

SUMMARY OF THE INVENTION

Composite laminate articles, comprising a metallic foil outer layer in which the surface of the metallic foil outer layer is modified to reflect a laser beam in a substantially diffuse manner, have been discovered to be useful as laser barriers. Such laser barriers can be used to protect the patient, operating room staff and operating room equipment from damage by laser beams used during laser surgical procedures.

The articles provide an economical laser barrier against penetration by most common laser wavelengths encountered in the clinical setting, including wavelengths in the range from the ultraviolet to the far infrared spectrum. The barrier can be formed into a surgical drape, eye shield, tape, or equipment/personnel shield, that protects against exposure to laser beam radiation in the clinical setting such as during surgical procedures that utilize a laser beam. The barrier protects the patient's underlying tissue by reflecting the laser beam and preventing contact of the underlying tissue with the beam, and protects surrounding equipment and personnel by diffusing the incident specular, intense, collimated light beam. The barrier retains a high degree of flexibility during surgical procedures even when impacted by laser beams. The article readily flexes, for example, for removal through the small incision made during minimal invasive procedures. The article maintains moisture in tissue and gauze dressings that lie beneath the laser barrier.

DESCRIPTION OF THE PREFERRED EMBODIMENTS

The present invention seeks to reduce the risk of injury and improve the level of safety during laser surgical procedures, protecting underlying tissue and surrounding equipment and personnel, by use of a barrier that disperses the incident specular collimated light beam and reflects it in multiple directions.

Figure 1:
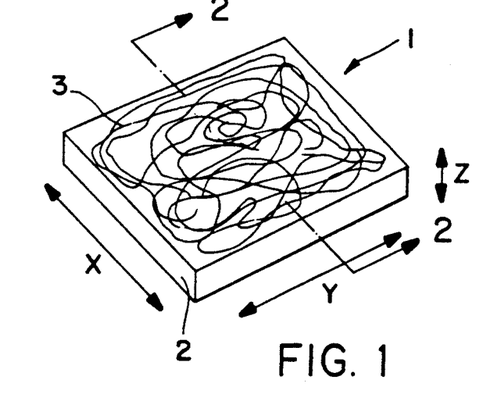
FIG. 1 is a perspective view of a laser barrier with a first type pattern.
Figure 2:
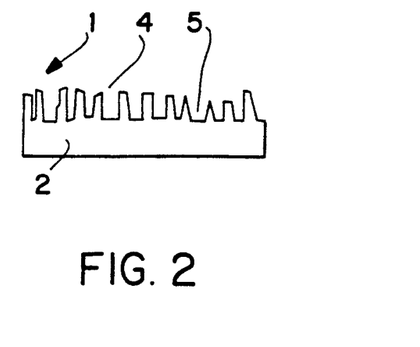
FIG. 2 is a partial sectional view taken along the line 2—2 of FIG. 1.

Referring to FIGS. 1 and 2 of the drawings, the laser barrier 1 in its simplest form, comprises a metal layer 2 which contains surface features 3 that provide a laser beam dispersing means of a "first type" pattern. Metal layer 2 is preferably composed of metals or alloys which are ductile, highly reflective of a wide range of wavelengths of incident radiation, nontoxic, and that have high melting points. The metal layers should have rigidity values of less than about 55,000 kg.mm and preferably less than about 8,000 kg.mm and most preferred less than 0.2 kg.mm. The metal layers should reflect at least 50% and preferably at least 95% of incident-laser radiation. Furthermore, preferred metals have melting temperatures of at least about 100° C.

The metal of layer 2 can be a foil of aluminum, cerium, cobalt, copper, gold, indium, iron, lead, molybdenum, neodymium, nickel, palladium, platinum, praseodymium, rhenium, rhodium, samarium, silver, tantalum, tin, titanium, tungsten, vanadium or zinc, and their alloys such as stainless steel. The preferred metal foils are aluminum, copper, gold, indium, nickel, niobium, palladium, palladium, platinum, rhenium, silver or titanium and alloys such as stainless steel. The most preferred metal foils include aluminum, nickel, gold, silver and stainless steel.

For laser barrier applications where the laser barrier is employed as a surgical drape, gown or eye shield, the thickness of metal layer 2 should be sufficient to resist puncture by laser beams for a reasonable period of time. For example, the metal layer must be capable of resisting puncture by a carbon dioxide laser having a 3 mm diameter focus and 5 watts of power for at least 0.2 second. The metal layer should be capable of resisting puncture by a carbon dioxide laser beam having a 0.6 mm diameter focus and 10 watts of power for at least one second, and more preferably for at least five seconds. However, the metal layer should also be thin enough to provide flexibility to the surgical drape, gown, or eye shield. The metal layer 2 routinely has a thickness between about $2.25 \times 10^{-3}$ mm and 1.5 mm. Preferably the thickness of the metal layer is between about $2.5 \times 10^{-3}$ mm and 1.0 mm, with the optimum thickness being between $5.0 \times 10^{-3}$ mm and 0.2 mm.

The surface features 3 of metal layer 2 provide a means for reflecting a laser beam in a disperse manner, as opposed to the more common specular reflection. The highly collimated and intense nature of the incident laser beam is fragmented in the dispersion process such that the reflected beam consists of many random low intensity beams. Although the sum total of energy of the reflected random beams is in principle equivalent to that of the incident specular collimated beam, the intensity of each reflected beam is greatly reduced by the dispersion process and the danger of injury is greatly reduced. The surface features 3 of metal layer 2 can be described as deviations or irregularities in surface geometry relative to a planar or mirror surface. Such irregularities can include any of a variety of surface patterns, or random features in the surface of metal layer 2 which provide a means for diffusing the laser beam. The surface irregularities 3 are typically produced on the surface of the metal layer by cutting, stamping, embossing, engraving, sanding, sandblasting, polishing, wire brushing, wet milling, or through other mechanical processes or through combinations of processes. Whatever the means or processes used, it is important that the reflective nature of the metallic surface be significantly retained to prevent absorption of the beam and melt-down of the metal. Other means of forming the surface features 3 may be used including chemical and two or more means may be combined with each other to form the surface features. The irregularities are shown in FIG. 2 as irregular protrusions 4 and recesses or indentations or voids 5.

Figure 11:
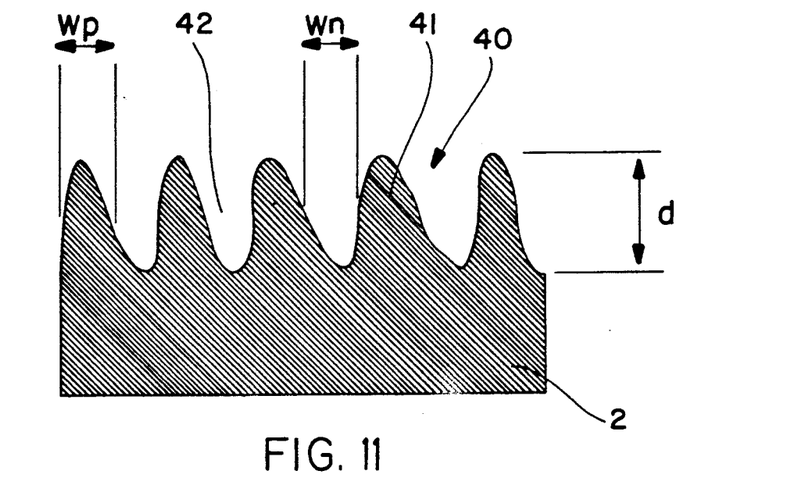
FIG. 11 is a partial sectional view of a laser barrier of the first type showing rounded intersecting surfaces.

For identification and evaluation purposes, the following symbols or descriptors have been adopted. The length is x and the width is y of the metal foil base, and the foil height is z. The intent is to essentially employ the use of the standard x,y,z plane concept. These are shown in FIG. 1. The depth of the given surface irregularity is d. It is the distance the protrusion of the irregularity extends above the remaining metallic base after the surface treatments. The average width of the protrusion or foil remaining in the treated area, after the surface treatment to form the irregularities, is Wp. Wp is the average width of the protrusions remaining on the treated area as measured in a cross-section taken in either the xz plane or in the yz plane. The average width of the individual foil voids or areas removed by the surface treatment in the treated area is Wn. Wn is the average width of the recesses formed in the foil between the protrusions as measured in a cross-section taken in either the xz plane or in the yz plane. These are shown in FIG. 11. The diameter of the laser beam directed onto or striking the metal foil is D and the wavelength of the laser beam is hv.

The diffuse reflective barrier of the invention consists of protrusions of various sizes and configurations. It is preferred that the recesses or voids and protrusions and base surfaces intersect with curved or rounded surfaces. Round surfaces present a continuously changing angle to the laser beam. Rounded surface intersections can be produced by controlling the manufacturing process. When manufacturing using the brush method, by selection of brush bristle diameter rigidity and length and control of the angle of contact, etc., the shape and depth caused by the abrasive action can be controlled as well as the shape of the intersecting surfaces. When manufacturing using the sand blasting method, by selection of the abrasion particles hardness, size and shape and the angle and speed of impact, etc., the shape and depth of abrasions can be controlled as well as the shape of the intersecting surfaces. The same controls can be applied to the other manufacturing processes to control the shape of the intersecting surfaces. The rounded intersections or corners can be seen in FIGS. 11-13. These intersecting surfaces are a representation of the barrier as determined by actual microscopic inspection of the barriers that can be produced by wire brushing, sand blasting and other means.

Even embossing with pyramidal shapes defined by flat surfaces and sharp corners, can produce the rounded intersections desired. For example, the flat surfaces and sharp corners are not faithfully replicated in the shape of the embossed surface of the foil. The resulting embossed surface shape depends on numerous factors. Visual and microscopic inspection of the surface features produced by a truncated pyramid embossing tool reveals that the intersecting surfaces are highly rounded, resembling bisected ellipses more than sharply defined intersecting flat surfaces. For best diffusive reflection the pressures and contact intensity can be controlled to yield the desirable curvature and maximize the ratio of curved surfaces to flat surfaces.

Figure 12:
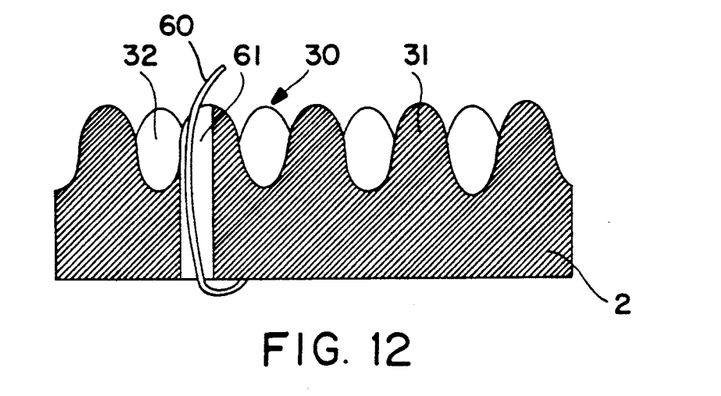
FIG. 12 is a partial sectional view of a laser barrier of the second type formed with alternate staggered rows of elliptical indentations and protrusions.

It is also possible to arrange or order the "periodicity" of the patterns so that the phases of individual surface features comprising rows and/or columns are staggered with respect to one another. Staggered patterns are preferred since they present greater variations of surface angles to the laser beam. These are shown in FIGS. 4, 6, 12 and 13. FIG. 12 depicts a metallic diffusion reflector 30 having an elliptical surface pattern with projections 31 and recessed areas 32 with alternating rows staggered to preclude an elongated channel.

Figure 13:
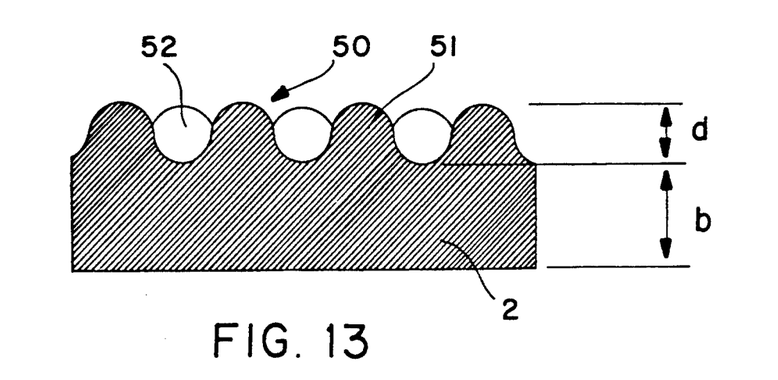
FIG. 13 is a partial sectional view of a laser barrier of the second type formed with alternate staggered rows of hemispherical surface indentations and protrusions.

FIG. 13 shows an embossing of the second type pattern 50 in the shape of hemispherical protrusions 51 and hemispherical recesses 52 in staggered rows. In this instance the depth d is essentially equal to the diameter of the sphere or twice its radius. The unaffected portion of the metallic reflector 2 or remaining base of the reflector is shown as b, the upper portion of which is referred to as the base plane of the metallic reflector. As shown in FIG. 13, by making a single embossment forming alternating hemispherical protrusions and recesses, a continuously changing angle can be presented to an incident laser beam. With this configuration of surface features, a structure is provided that can cause a beam angle diffusion that approaches the diffusion of the gas blown bubble structure disclosed in applicant's prior application. With this configuration, a specific ratio can be selected between the hemisphere diameter and the laser beam diameter to give a fairly accurate control of the strength of the reflected beams. Because of the continuously changing angles, the reflections are fairly uniform for different angles of incidence of the laser beams onto the barrier layer surface as compared to the random patterns resulting from brushing, sand blasting, etc.

The desired pattern depth d is related to the laser wavelength hv. The acceptable range is $1,000 \text{ hv} > d > \text{hv}/4$, the preferred range is $500 \text{ hv} > d > \text{hv}/2$, and the optimum range is $200 \text{ hv} > d > \text{hv}$. The wavelength hv can range between about 0.2 microns and 20 microns, and most typically falls between 0.3 microns and 10.6 microns for surgical lasers. In order to effectively diffuse the incident laser beam, surface irregularities must have an adequate depth d. Typically d should be at least one fourth the depth of the wavelength of the laser beam that the laser barrier is intended to protect against. It is preferred that the depth be at least one half the depth of the wavelength of the laser beam. It is optimum that the depth be greater than the wavelength of the laser beam. The depth should range from about 0.075 microns to 10,000 microns, with a preferred range of from 15 microns to 500 microns and an optimum range being from 0.3 microns to 250 microns. As a practical application, a depth of 10,000 microns would require an article so thick it would not have the desired drapability. It is only for this reason that the preferred and optimum maximum ranges are not larger.

The desired average width of the protrusions Wp formed in the foil is related to the diameter of the laser beam D. The acceptable range is $1 \text{ micron} < Wp < D$, the preferred range is $2 \text{ micron} < Wp < D/2$, and the optimum range is $2 \text{ microns} < Wp < D/4$. The beam diameter D varies depending on the specific laser used, but typically ranges from 100 to 1000 microns and usually from 200 to 500 microns. Therefore it is acceptable that protrusion Wp be within the range of about 1 to 1000 microns; it is preferable that Wp be within the range of about 2 to 200 microns; and optimum for Wp to be within the range of about 2 to 100 microns.

The desired average width of the recesses Wn formed in the foil between the protrusions is related to the average protrusion width Wp. As the widths Wp and Wn approach the same value, a desirably dense pattern results. This density in the pattern is most effective in converting the collimated incident beam into diffuse reflections of low energy beams. The acceptable range is $Wp \times 5 > Wn > Wp \times 0.20$, with the preferred range being $Wp \times 3 > Wn > Wp \times 0.33$, with the optimum range being $Wp \times 2 > Wn > Wp \times 0.50$. As a result of the relationship between the diameters Wp and Wn, the void diameter Wn can range between 0.2 microns and 5000 microns. It is preferable that the void diameter Wn range between 0.66 microns and 600 microns. It is optimum for the diameter Wn to range between 1 micron and 200 microns.

An alternate way to determine the amount of metal removed from the metal layer 2 is to measure the surface area of the metal layer before any material has been removed and then measure the remaining area of the surface after treatment to determine the ratio or percentage of the original surface area that has been removed. It is desirable that the original surface area removed be from 20 to 80% of the total original surface area. It is preferred that the removed area range from 35 to 65% with the optimum removal being from 40 to 60%.

In a preferred embodiment of the invention the diffuse surface feature means are represented by a combination or overlay of at least two patterns that co-exist on the surface of metal layer 2 which is intended to be contacted with the incident laser beam. The first type of two patterns is a pattern consisting of lines, holes, voids or other shapes which are regular or irregular in nature, which can be defined as voids or spaces that usually result from the removal of metal from the surface of metal layer 2. As shown in FIGS. 2 and 11, features 3,40 defined by the protrusions 4,41 and voids or spaces 5,42 have a depth d relative to the untreated surface area or the base plane of metal layer 2.

Figure 3:
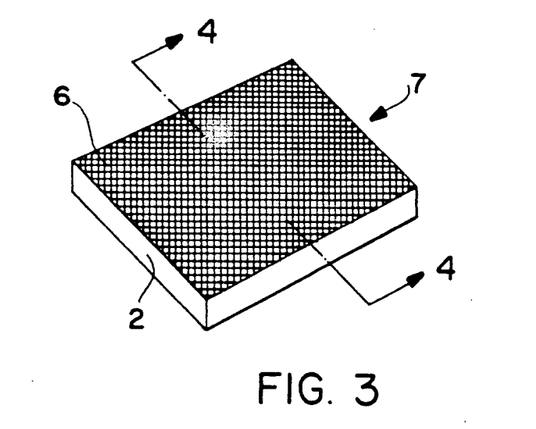
FIG. 3 is a perspective view of a laser barrier with a second type pattern.
Figure 4:
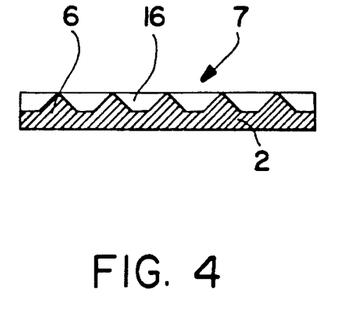
FIG. 4 is a partial sectional view taken along the line 4—4 of FIG. 3.

The "second type" of two general types of patterns, which can be used independently or coexist as overlaid or combined patterns with the first type pattern on the surface of metal layer 2, is a pattern with dimensions larger than the first. The second type of pattern is depicted in FIGS. 3 and 4 as a laser beam dispensing barrier 7. FIG. 4 depicts an embossing of the second type pattern 7 consisting essentially of elongated linear pyramids on the metallic reflector 2 that intersect perpendicularly to each other to form a grid of projection 6 with recessed areas 16. The dimensions are described by the same depth, width and length of the surface features shown in FIGS. 1 and 11. The depth d of the pattern typically accounts for the extent the surface feature 4 rises above the x/y base plane of the metal layer 2.

Figure 5:
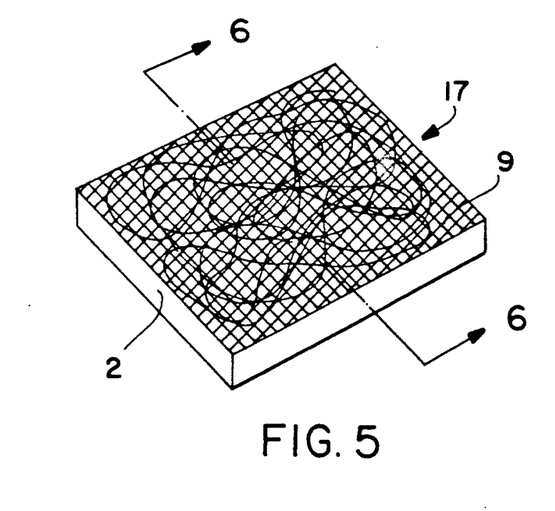
FIG. 5 is a perspective view of a laser barrier with a first type pattern superimposed over a second type pattern.
Figure 6:
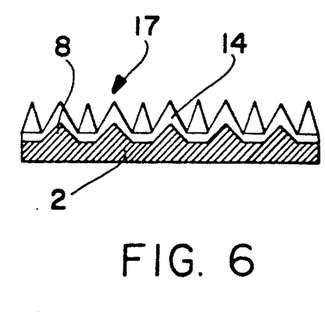
FIG. 6 is a partial sectional view taken along the line 6—6 of FIG. 5.

The combination of the finer and coarser surface features or patterns, described as the first type and second type, are combined to produce surface feature 9, which constitutes a preferred embodiment of this invention. They are depicted in FIGS. 5 and 6 as a laser barrier 17. Within the dimensions set forth for the patterns, the shape, size and distribution of the features 9, which make up the combined "first type" and "second type" patterns, can vary considerably. The superimposed patterns as shown in FIG. 6, can be pyramids, ellipses, hemispheres or alternative shaped patterns 6 providing changing angles having superimposed thereon fine patterns 14. FIG. 6 depicts projections 8 in the shape of truncated pyramids embossed onto a metallic reflector 2 having alternating rows staggered forming a second type pattern and superimposed on the second type pattern 8 a first type pattern 14 that forms a composite 17 of the two pattern types.

As a result of the practical manufacturing limitations, first type patterns are typically available with depth values d and void values Wn and protrusions Wp smaller than those typically used for second type patterns. First type patterns were discovered to be most effective for dispersing laser beams with wavelengths from 0.3 microns to 9 microns. Second type patterns, possessing typically larger void diameters Wn and depth values d, were discovered to be most effective for lasers operating at wavelengths of 10 microns and longer. Superimposing the first and second type patterns provides a laser barrier that effectively diffuses the incident beam of all lasers that are typically employed in the surgical environment. These superimposed patterns are hereafter referred to as a Universal Wavelength Laser Barrier.

To achieve a Universal Laser Barrier, the protrusions Wp for first type patterns, typically average from about 1 to 200 microns, with a preferred range of from 2 microns to 80 microns and an optimum range of from 2 microns to 40 microns. The spacing between protrusions Wn for random type patterns typically can range, according to the relationship between Wp and Wn, on the average from about 0.2 to about 1000 microns, with a preferred range of from 0.66 to 240 microns, and an optimum range of from 1 to 80 microns. The protrusions Wp for the second type patterns typically range an average of from about 10 to 1000 microns, with a preferred range of from 11 microns to 200 microns, and an optimum range of from 12 microns to 100 microns. The spacing between protrusions Wn for random type patterns typically can range, according to the relationship between Wp and Wn, on the average from about 2 to about 5000 microns, with a preferred range of from 3.6 to 600 microns, and an optimum range of from 6 to 200 microns.

To achieve a Universal Laser Barrier resulting from the superimposition of patterns of the first type and the second type, the respective surface features should have the following ranges of depth d. Patterns of the first type should range on the average from about 0.5 to 12 microns in depth, with a more preferred depth of 1 to 10 microns and optimum depth of from 2 to 9 microns. Patterns of the second type should have a depth range on the average from about 3 microns to about 1000 microns, with a preferred depth of 6 to 500 microns, and an optimum depth of from 11 to 200 microns. Superimposition of these first type and second type patterns on a metal layer have been discovered to be useful against surgical laser operating wavelengths from approximately 0.3 to approximately 10.6 microns. These wavelengths include as examples: the excimer laser (about 0.3 microns), Argon laser (about 0.5 microns), KTP laser (about 0.5 microns), Nd-YAG laser (about 1.1 microns), Ho-YAG laser (about 2.1 microns) and carbon dioxide laser (about 10.6 microns). The laser barrier functions by resisting beam penetration and reflecting the collimated incident beam in a diffuse manner. The barriers are flexible and can be backed with absorbent material, adhesive means, reinforcing film and can have other modifications made to them.

The laser shields of this invention are able to resist puncture by all commonly used carbon dioxide, argon, KTP and Neodymium YAG lasers for at least two seconds, and generally for greater than five seconds. The laser shields of this invention reflect the incident beam in a diffuse mode as opposed to a high intensity, specular mode as illustrated by the following examples.

EXAMPLE 1

Aluminum foil of a thickness of 0.075 mm which has a "scratch brush" finish consisting of extended random lines approximately 0.5 microns deep and 0.5 microns in thickness, and occupying approximately 35% of the available surface area (as determined by microscopic inspection), was cut into a shape of 30 cm×45 cm. The unfinished side was sprayed with an acrylate-based pressure sensitive adhesive obtained from 3M Company, which was allowed to stand for approximately 30 seconds. The tacky adhesive surface was covered with a 25 cm×40 cm piece of cotton gauze with a thickness of about 0.3 mm, such that the pressure sensitive adhesive was allowed to extend 2.5 cm around the periphery of the gauze on all sides. Such laser barrier is intended for use as a laser resistant surgical drape.

EXAMPLE 2

A laser barrier was constructed in accordance with Example 1 except that the scratch brush aluminum foil was embossed with a truncated square base pyramid design, whereby each pyramid character had a height of approximately 0.02 mm and base dimensions of approximately 0.20 mm×0.20 mm. The spacing between each character was approximately 0.20 mm.

EXAMPLE 3

A laser barrier was constructed in accordance with Example 2 except that common mill finish aluminum foil was employed. The aluminum foil was disposed such that the shiny or smooth side faced upwards and embossed.

EXAMPLE 4

A laser barrier was constructed in accordance with Example 3 except that the embossing pattern consisted of truncated square pyramids with a base of 0.1 mm×0.1 mm and a height of 0.02 mm. The base of each pyramid abutted the neighboring pyramids on each side.

EXAMPLE 5

A laser barrier was constructed in accordance with Example 2 except that the adhesive was obtained from Flexcon and applied as film that was carried on a transfer tape. The tape consisted of a 0.025 mm polyethylene film coated on each side with 0.025 mm of acrylate-based pressure sensitive adhesive.

EXAMPLE 6

A laser barrier was constructed in accordance with Example 2 except that the adhesive employed was a silicone-based pressure sensitive adhesive available from Dow Corning ("BIO-PSA ® Medical Grade Silicone Pressure Sensitive Adhesive).

The laser barriers of Examples 1–6 were exposed to a laser beam. The beam was 400 microns in diameter and produced by a carbon dioxide laser having 40 watts in power. The laser struck the samples at a 90° angle. Laser exposure time was 10 seconds. The ability to resist penetration by the laser beam is compared to cotton gauze and unfinished, common aluminum foil as obtained from the mill.

| Material | Time to Puncture | Appearance on side towards laser |
| --- | --- | --- |
| Example 1 | >10 seconds | no change |
| Example 2 | >10 seconds | no change |
| Example 3 | >10 seconds | no change |
| Example 4 | >10 seconds | no change |
| Example 5 | >10 seconds | no change |
| Example 6 | >10 seconds | no change |
| aluminum foil (smooth mill finish) | >10 seconds | no change |
| cotton gauze (.2 mm thickness) | <0.1 seconds | .5 mm diameter hole |

Reflectivity of the laser barriers containing the surface modification to the aluminum foil of Examples 1–6 were compared to aluminum foil which is smooth and unmodified. The laser beam was 400 microns in diameter and produced by a carbon dioxide laser having 40 watts in power. The laser struck the samples at a 45° angle. Laser exposure time was 10 seconds. Thermal paper was placed at varying distances from the laser barrier along the reflected beam path (assuming specular reflection) and time to blacken the paper was noted.

| Material | Distance | Time to blacken |
| --- | --- | --- |
| Example 1 | 70 cm | >10 seconds |
| Example 1 | 20 cm | 2.0 seconds |
| Example 2 | 70 cm | >10 seconds |
| Example 2 | 20 cm | >10 seconds |
| Example 3 | 70 cm | >10 seconds |
| Example 3 | 20 cm | 4.0 seconds |
| Example 4 | 70 cm | >10 seconds |
| Example 4 | 20 cm | 5.5 seconds |
| Example 5 | 70 cm | >10 seconds |
| Example 5 | 20 cm | >10 seconds |
| Example 6 | 70 cm | >10 seconds |
| Example 6 | 20 cm | >10 seconds |
| aluminum foil | 70 cm | 0.6 seconds |
| aluminum foil | 20 cm | 0.1 seconds |

The laser barriers of Examples 1 through 6, which encompass the diffuse reflective surface means of the present invention, did not blacken the thermal paper placed in the reflected beam path (assuming specular reflection) at 70 cm. Examples 2, 5 and 6, which represent a preferred embodiment of the present invention, did not blacken the thermal paper placed in the reflected beam path at 20 cm. Aluminum foil which did not possess the surface feature diffuse reflective means of the present invention, strongly reflected the laser beam in specular fashion and thus rapidly blackened the thermal paper.

The barrier of Examples 1, 2 and 4 were exposed to the beam of a Neodymium YAG laser. The laser beam had a diameter of 250 microns at the target and the laser had a power of 60 watts. The laser was set to the continuous mode of operation for 10 seconds. The angle of the incident beam was 90°.

| Material | Time to Puncture | Appearance on side towards laser |
| --- | --- | --- |
| Example 1 | >10 seconds | no change |
| Example 2 | >10 seconds | no change |
| Example 4 | >10 seconds | no change |

-continued

| Material | Time to Puncture | Appearance on side towards laser |
|---|---|---|
| Aluminum foil | >10 seconds | no change |

Reflectivity of the laser barriers containing the surface modifications to the aluminum foil of Examples 1, 2 and 3 was compared to aluminum foil which is smooth and unmodified. The laser beam was 250 microns in diameter and produced by a Neodymium YAG laser having 60 watts of power. The laser struck the samples at a 45° angle. The "% Specular Reflection" was determined by measuring the reflected beam power across the beam diameter. The ratio of the observed power per unit area versus the theoretical power per unit area, assuming a mirror surface, was calculated and multiplied by 100 to give "% Specular Reflection."

| Material | % Specular Reflection |
|---|---|
| Example 1 | 15% |
| Example 2 | 9% |
| Example 3 | 84% |

The results illustrate that the present invention has the ability to substantially reduce the specular reflection of the laser beam produced by a Neodymium YAG laser.

The following examples further demonstrate the effectiveness of the novel laser barriers incorporating patterns of the first type on a metal layer, and the effectiveness of the novel laser barriers incorporating patterns of the second type, and also the effectiveness of the preferred embodiment of the invention, a Universal Laser Barrier, which superimposes the patterns of the first type and the patterns of the second type onto the metal layer.

EXAMPLE 7

Preparation and Testing of a Laser Barrier

Incorporating a "First Type" Pattern

A standard mill grade aluminum foil (alloy 1145) of a thickness of 0.075 mm was treated by an abrasive process to produce a surface pattern consisting of extended random recesses which ranged from approximately 1 to 10 microns in depth d, the average being about 2 microns; the voids or recesses ranged from about 2 to 25 microns in width Wn, the average being about 4 microns; the cross-sectional width of the protrusions Wp between the recesses ranged from less than 1 micron to approximately 40 microns; the average being approximately 10 microns. The untreated side of the foil was sprayed with an acrylate-based pressure sensitive adhesive obtained from 3M Company, which was allowed to stand for approximately 30 seconds. The tacky adhesive surface was then covered with a 25 cm×40 cm piece of cotton gauze with a thickness of about 0.3 mm. The pressure sensitive adhesive was allowed to extend 2.5 cm around the periphery of the gauze on all sides. This is the type laser barrier intended for use as a laser resistant surgical drape.

This laser barrier was tested utilizing an Argon laser (hv=0.5 microns, power=5 watts, continuous beam, 250 micron D), a Nd-YAG laser (hv=1.1 microns, power=70 watts, 0.5 sec pulsed beam, 300 micron D) and a carbon dioxide laser (hv=10.6 microns, power=50 watts, continuous beam, 350 micron D). The exposure of the respective laser beams was for 10 seconds. The relative positioning of the laser beam was at 45 and 90 degree angles relative to the surface plane x/y of the barrier.

The laser beams did not penetrate the laser barrier.

The reflected beams were measured at an incidence angle of 45 degrees. A power detector was utilized to estimate the specular and diffuse reflection components, relative to the reflection produced by a smooth, mirror-like aluminum foil, employed as a standard of comparison calibrated as reflecting in a 100% specular mode. The resulting diffusion (% diffusion reflection/% specular reflection) was:

| | Argon | Nd-YAG | carbon dioxide |
|---|---|---|---|
| Standard foil | 0/100 | 0/100 | 0/100 |
| Sample | 96/4 | 88/12 | 57/43 |

EXAMPLE 8

Preparation and Testing of a Laser Barrier

Incorporating a "Second Type" Pattern

A standard mill grade aluminum foil (alloy 1145) of a thickness of 0.075 mm was embossed with a tool that imparted a surface pattern consisting of alternating rows of essentially bisected ellipses 20 microns in depth d; such bisected ellipses having an average diameter Wp of about 100 microns; and an average spacing distance Wn from one another of about 50 microns. The untreated side was sprayed with an acrylate-based pressure sensitive adhesive obtained from 3M Company, which was allowed to stand for approximately 30 seconds. The tacky adhesive surface was covered with a 25 cm×40 cm piece of cotton gauze with a thickness of about 0.3 mm, such that the pressure sensitive adhesive was allowed to extend 2.5 cm around the periphery of the gauze on all sides. This also is the type laser barrier intended for use as a laser resistant surgical drape.

This laser barrier was tested utilizing an Argon laser (hv=0.5 microns, power=5 watts, continuous beam, 250 micron D), a Nd-YAG laser (hv=1.1 microns, power=70 watts, 0.5 sec pulsed beam, 300 micron D) and a carbon dioxide laser (hv=10.6 microns, power=50 watts, continuous beam, 350 micron D). Exposure of the respective laser beams was for 10 seconds. The relative positioning of the laser beam was at 45 and 90 degree angles relative to the surface plane (x/y) of the barrier.

The laser beams did not penetrate the laser barrier.

The properties of the reflected beams were measured at an incidence angle of 45 degrees. A power detector was utilized to estimate the specular and diffuse reflection components relative to the reflection produced by a smooth, mirror-like aluminum foil which was employed as a standard of comparison and which was calibrated as reflecting in a 100% specular mode. The resulting diffusion (% diffuse reflection/% specular reflection) was:

| | Argon | Nd-YAG | carbon dioxide |
|---|---|---|---|
| Standard foil | 0/100 | 0/100 | 0/100 |
| Sample | 69/31 | 83/17 | 91/9 |

EXAMPLE 9

Preparation and testing of a "Universal Laser Barrier" Incorporating a "Second Type" Pattern Superimposed Over a "First Type" Pattern A standard mill grade aluminum foil (alloy 1145) of a thickness of 0.075 mm was abrasion treated on the front surface according to Example 7. The resulting aluminum foil was then treated according to Example 8, such that the embossing tool contacted the non-abraded surface, thus preserving the first type pattern while superimposing the resulting second type Pattern on the front surface. The resulting surface possessed substantially the superimposed random line pattern of Example 7 and the alternating bisected ellipse pattern of Example 8. The non-superimposed side or rear surface was sprayed with an acrylate-based pressure sensitive adhesive obtained from 3M Company, which was allowed to stand for approximately 30 seconds. The tacky adhesive surface was covered with a 25 cm×40 cm piece of cotton gauze with a thickness of about 0.3 mm, such that the pressure sensitive adhesive was allowed to extend 2.5 cm around the periphery of the gauze on all sides. This also is the type laser barrier intended for use as a laser resistant surgical drape.

This laser barrier was tested utilizing an Argon laser (hv=0.5 microns, power=5 watts, continuous beam, 250 micron D), Nd-YAG laser (hv=1.1 microns, power=70 watts, 0.5 sec pulsed beam, 300 micron D) and a carbon dioxide laser (hv=10.6 microns, power=50 watts, continuous beam, 350 micron D). Exposure of the respective laser beams was for 10 seconds. The relative positioning of the laser beam was at 45 and 90 degree angles relative to the surface plane (x/y) of the barrier.

The laser beams did not penetrate the laser barrier.

The properties of the reflected beams were measured at an incidence angle of 45 degrees. A power detector was utilized to estimate the specular and diffuse reflection components relative to the reflection produced by a smooth, mirror-like aluminum foil which was employed as a standard of comparison and which was calibrated as reflecting in a 100% specular mode. The resulting diffusion (% diffuse reflection/% specular reflection) was:

|  | Argon | Nd-YAG | carbon dioxide |
| --- | --- | --- | --- |
| Standard foil | 0/100 | 0/100 | 0/100 |
| Sample | 98/2 | 99/1 | 97/3 |

These examples demonstrate the utility of the laser barriers of the present invention. Laser barriers incorporating surface features of the first type patterns have shown a meaningful and desirable improvement in reduction of specular reflectance and increase in diffuse reflectance compared with unmodified aluminum foil. Such laser barriers with the first type patterns are particularly effective with the shorter wavelength surgical lasers, although a meaningful but less substantial improvement is also observed in the longer wavelength lasers. Laser barriers incorporating surface features of the second type patterns have shown a meaningful and desirable improvement in reduction of specular reflectance and increase in diffuse reflectance compared with unmodified aluminum foil. Such laser barriers of the second type patterns are particularly effective with the longer wavelength surgical lasers, although a meaningful but less substantial improvement is also observed in the shorter wavelength lasers. A laser barrier, comprised of a metal layer incorporating surface features, resulting from superimposition of patterns of the first type and the second type provides for a laser barrier which reflects laser beams over a wide range of wavelengths in a substantially diffuse manner.

Figure 7:
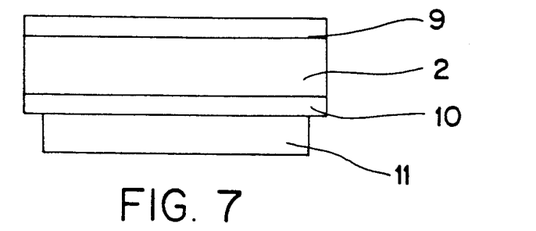
FIGS. 7-9 are partial sectional views of the laser barrier shown in FIGS. 5 and 6 combined with gauze and adhesive means ready for use.

A preferred embodiment of the present invention for surgical use is illustrated in FIG. 7 and includes a fabric sheet 11 laminated to the underside of metal layer 2 by an adhesive layer 10. The metal surface is shown having superimposed patterns 9, as depicted in FIG. 5. When in use, fabric sheet 11 is placed in contact with the skin of the patient resulting in a laser barrier that is safer than laser barriers which have metal layer 2 in contact with the patient.

It is preferred that the fabric sheet 11 be made, at least on the exterior surface, of non-thermoplastic fibers, such as wood pulp and rayon or other non-thermoplastic materials such as woven or knit muslin, cotton or silk. The non-thermoplastic materials do not melt when the laser barrier is struck by a laser beam, and act as an insulating layer protecting the tissue of the patient from the laser beam.

Figure 10:
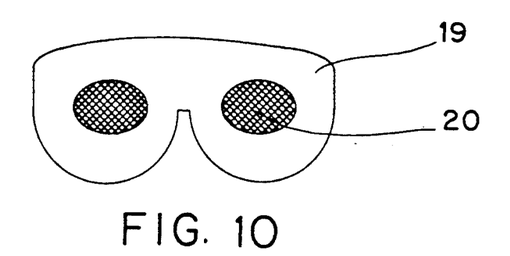
FIG. 10 is a bottom plan view of a laser barrier in the shape of an eye shield.

In cases where the laser barrier is used as a surgical drape, the preferred fabric sheet 11 is "Steri-Drape ® Blue Fabric" sold by 3M Company or non-woven fabric grade 7887 sold by The Dexter Company. In cases where the laser barrier is used as a drape formed in the shape of an eye shield the preferred fabric sheet 11 is "Large Eye Pad #8772" sold by Johnson & Johnson Medical Inc. FIG. 10 depicts the laser barrier formed in the shape of an eye shield. The eye shield 19 is shown with pads 20 for contacting the eyes.

Figure 8:
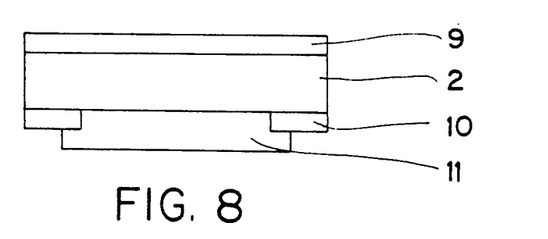

As shown in FIG. 7, metal layer 2 and fabric sheet 11 can be laminated together over their entire juxtaposed surfaces by adhesive layer 10. However, an alternative preferred embodiment, illustrated in FIG. 8, is to bond the metal layer 2 and fabric sheet 11 with an adhesive layer 10, disposed only along the periphery.

Figure 9:
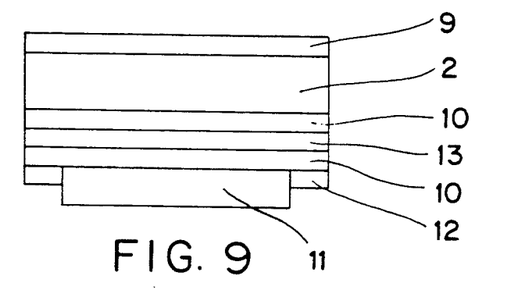

Another embodiment of the present invention for use as a laser barrier which is employed as a surgical drape or eye shield, is illustrated in FIG. 9 and includes a polymeric film layer 13 disposed between metal layer 2 and fabric sheet 11. Such intermediate layer of polymeric film 13 has been found useful to protect the thin metal layer 2 from damage during handling. Suitable polymeric films include polyester, polyurethane, polyamide, polycarbonate, polypropylene and polyethylene. Preferably polymeric film layer 13 has a thickness of between 0.005 mm and 0.20 mm. The polymeric film layer 13 can be adhered to the metal layer 2 by extrusion of layers. Alternatively, the polymeric film layer 13 can be adhered to the metal layer 2 by use of an adhesive. The underside of polymeric film layer 13 can be adhered to fabric sheet 11 with an adhesive 10. One embodiment of the present invention utilizes a double sided adhesive transfer tape consisting of a polymeric layer 13 which is coated with pressure sensitive adhesive 10 on both sides. The adhesive sides are used to bond the polymeric layer 13 to metal layer 2 and fabric sheet 11 respectively. Preferred pressure-sensitive adhesives employed in the double sided adhesive transfer tape are silicone-based adhesives and acrylate-based adhesives. Suitable double sided adhesive transfer tapes are available from the Specialty Tapes Division of RSW Inc., Racine, Wis. and Flexcon, Spencer, Mass. To protect the adhesive, a release layer 12 is removably attached over the exposed adhesive 10.

The construction of the present invention may include a pressure-sensitive adhesive on portions of the patient side of the laser barrier to aid in positioning the laser barrier on the patient and maintaining a tight seal to prevent incident laser radiation from entering under the barrier. The pressure sensitive adhesive may be applied to the fabric sheet 11 or may be directly applied to metal layer 2. Preferred pressure-sensitive adhesives include silicone-based adhesives and acrylate-based adhesives. A particularly-preferred pressure sensitive adhesive is an isooctylacrylate acid copolymer commercially available as "Medical Transfer Adhesive No. 1524" from 3M Co. Another particularly-preferred pressure sensitive adhesive available in film form is "Dermaflex TT-200" from Flexcon, Spencer Mass. A release liner 12, shown in FIG. 9, normally made of coated paper or plastic film, is typically employed to cover the pressure sensitive adhesive. Prior to use, the release liner is peeled away by the user exposing the pressure sensitive adhesive, and enabling attachment by pressing the adhesive to the patient in the area to be protected.

Laser barriers of this invention employed as surgical drapes can also be designed to include other conventional provisions such as those that accommodate accessories. The drape may be designed with instrument pouches, fluid control pouches, apertures, etc.

For surgical applications, the laser barrier is cut to the desired shape, adhesive is applied to the patient side as needed, and the drape is sterilized after packaging. The laser-resistant drape may be safely used, either wet or dry, in areas where laser energy is being applied to a patient so as to shield the patient from unintended laser radiation such as might occur by the accidental movement of the laser source or the patient.

The laser beam reflector can be used inside a body cavity, either a naturally occurring cavity or one formed by an incision. To use the reflector inside such a cavity, it can be folded or rolled-up, inserted into the cavity access opening or through the incision, and then manipulated to place it over or around the area to be protected. To assist removal, an elongated flexible means, such as a naturally occurring, plastic, or metallic string 60 can be inserted through a hole 61 in the reflector. The reflector can then be removed by pulling on the string 60, with or without folding or rolling the reflector prior to pulling on the string depending on the location and size of the access opening.

The laser barriers of the present invention provide protection against both laser penetration and direct or specular reflection. Consequently, the laser barriers directly protect the patient from the laser beam and indirectly protect those in the operating room from the reflected laser beam. Upon making contact with the laser beam, the laser barriers of the present invention cause the beam to be reflected in a diffuse manner, greatly reducing the hazard of the laser beam.

It is believed that the construction, operation and advantages of this invention will be apparent to those skilled in the art. It is to be understood that the present disclosure is illustrative only and that changes, variations, substitutions, modifications and equivalents will be readily apparent to one skilled in the art and that such may be made without departing from the spirit of the invention as defined by the following claims.

I claim:
1. A reflector for diffusing a laser beam including:
   a metallic layer;
   said metallic layer having surface features for dispersing an incident laser beam in plural directions;
   said surface features including irregularities in the form of protrusions and indentations;
   said protrusions rising an average of from 0.3 to 10,000 microns above said metallic layer base and having an average diameter of from 1 to 1,000 microns;
   said indentations between said protrusions having an average width of from 0.2 to 5,000 microns.
2. A reflector for diffusing a laser beam as described in claim 1 wherein:
   said protrusions rise an average of 0.3 to 500 microns and have an average diameter of from 2 to 200 microns;
   said indentations have an average width of from 0.66 to 600 microns.
3. A reflector for diffusing a laser beam as described in claim 1 wherein:
   said protrusions rise an average of 0.3 to 10 microns and have an average diameter of from 2 to 40 microns;
   said indentations have an average width of from 1 to 80 microns.
4. A reflector for diffusing a laser beam as described in claim 1 wherein:
   said protrusions rise an average of 10 to 100 microns and have an average diameter of from 20 to 100 microns;
   said indentations have an average width of from 20 to 200 microns.
5. A reflector for diffusing a laser beam as described in claim 1 wherein:
   said protrusions are in the form of truncated pyramids.
6. A reflector for diffusing a laser beam as described in claim 5 wherein:
   the intersecting surfaces of said pyramids and the intersecting surfaces of said pyramids and said metallic base are rounded.
7. A reflector for diffusing a laser beam as described in claim 1 wherein:
   said protrusions are in the form of hemispheres and said indentations are in the form of hemispheres.
8. A reflector for diffusing a laser beam as described in claim 7 wherein:
   said hemispheres have a radius of from 5 microns to 1,000 microns.
9. A reflector for diffusing a laser beam as described in claim 1 wherein:
   said protrusions and said indentations are in the form of ellipses.
10. A reflector for diffusing a laser beam as described in claim 1 wherein:
    said protrusions are in the form of elongated pyramids that extend parallel and perpendicular to one another so as to form a grid.
11. A reflector for diffusing a laser beam as described in claim 10 wherein:
    the intersecting surfaces of said elongated pyramids and the intersecting surfaces of said metallic base are rounded to present a continuously changing angle to incident laser beams.
12. A reflector for diffusing a laser beam as described in claim 1 wherein:

the intersecting surfaces of said protrusions and the intersecting surface of said protrusion with said metallic layer base are rounded to present a continuously changing angle to incident laser beams.

13. A reflector for diffusing a laser beam as described in claim 1 wherein:
said surface features for dispersing an incident laser beam into plural directions includes a first type pattern superimposed on a second type pattern with said first type pattern being formed from smaller depth protrusions and spacings than those of said second type pattern.

14. A reflector for diffusing a laser beam as described in claim 13 wherein:
said first type pattern consists of protrusions that have average heights from 0.3 to 10 microns and average widths of from 2 to 40 microns and average spacings between said protrusions of from 1 to 80 microns and said second type pattern consists of protrusions that have average heights of from 10 to 150 microns and average widths of from 20 to 100 microns and average spacings between said protrusions of from 20 to 200 microns.

15. A reflector for diffusing a laser beam as described in claim 1 wherein:
said metallic layer has a backing of gauze attached to it for protecting the objects over which it is placed.

16. A reflector for diffusing a laser beam as described in claim 1 wherein:
said metallic layer is aluminum.

17. A reflector for diffusing a laser beam as described in claim 1 wherein:
said metallic layer has attached thereto an adhesive layer for attachment to a surface to be protected.

18. A reflector for diffusing a laser beam as described in claim 1 wherein:
said metallic layer has attached thereto an elongated flexible means for pulling said reflector.

19. A process for using a reflector for diffusing a laser beam including:
providing a metallic reflector for diffusion of a laser beam wherein said metallic reflector surface has irregularities in the form of protrusions and indentations with said protrusions rising an average of from 0.3 to 500 microns above said metallic layer base and having an average diameter of from 2 to 200 microns with said indentations between said protrusions having an average width of from 0.6 to 600 microns;
reducing the size of said reflector by folding or rolling said reflector;
inserting said reflector through an opening;
unfolding or unrolling said reflector and placing it over an area to be protected from a laser beam.

20. A process for using a reflector for diffusing a laser beam as described in claim 19 including:
attaching an elongated flexible means to said reflector;
pulling on said elongated flexible means to remove said reflector through said opening.

* * * * *